(12) United States Patent
Chen et al.

(10) Patent No.: US 10,569,252 B2
(45) Date of Patent: Feb. 25, 2020

(54) UTSA-74: A METAL ORGANIC FRAMEWORK WITH TWO ACCESSIBLE BINDING SITES PER METAL CENTER FOR GAS SEPARATION AND GAS STORAGE

(71) Applicants: The Board of Regents of the University of Texas System, Austin, TX (US); East China Institute of Technology, Fuzhou, Jiangxi (CN)

(72) Inventors: Banglin Chen, San Antonio, TX (US); Feng Luo, Jiangxi (CN)

(73) Assignees: THE BOARD OF REGENTS OF THE UNIVERSITY OF TEXAS SYSTEM, Austin, TX (US); EAST CHINA INSTITUTE OF TECHNOLOGY, Jiangxi (CN)

( * ) Notice: Subject to any disclaimer, the term of this patent is extended or adjusted under 35 U.S.C. 154(b) by 232 days.

(21) Appl. No.: 15/494,449

(22) Filed: Apr. 22, 2017

(65) Prior Publication Data
US 2017/0341055 A1 Nov. 30, 2017

Related U.S. Application Data

(60) Provisional application No. 62/326,385, filed on Apr. 22, 2016.

(51) Int. Cl.
| | | |
|---|---|---|
| *B01D 53/02* | (2006.01) |
| *B01J 20/22* | (2006.01) |
| *B01J 20/30* | (2006.01) |
| *C07C 65/05* | (2006.01) |
| *C07C 7/12* | (2006.01) |
| *C01B 32/50* | (2017.01) |

(52) U.S. Cl.
CPC ............ *B01J 20/226* (2013.01); *B01D 53/02* (2013.01); *B01J 20/3085* (2013.01); *C01B 32/50* (2017.08); *C07C 7/12* (2013.01); *C07C 65/05* (2013.01); *B01D 2253/204* (2013.01); *B01D 2256/22* (2013.01); *B01D 2257/7022* (2013.01)

(58) Field of Classification Search
CPC .......... B01D 2253/204; B01D 2256/22; B01D 2257/504; B01D 2257/7022; B01D 53/02; B01J 20/226; B01J 20/3085; C01B 32/50; C01B 39/00; C07C 65/05; C07C 7/12; Y02C 10/08; Y02P 20/152
See application file for complete search history.

(56) References Cited

U.S. PATENT DOCUMENTS

| | | | |
|---|---|---|---|
| 8,664,419 B2 | 3/2014 | Chen | |
| 2011/0144367 A1* | 6/2011 | Hupp | ...................... C07F 3/003 556/121 |
| 2011/0269984 A1* | 11/2011 | Chen | ...................... C07C 65/05 556/49 |
| 2013/0068075 A1 | 3/2013 | Stiebitz et al. | |
| 2013/0096210 A1* | 4/2013 | Yaghi | ..................... B01J 20/226 514/784 |
| 2014/0179514 A1* | 6/2014 | Matzger | ............... B01J 20/3085 502/165 |
| 2015/0173368 A1* | 6/2015 | Morris | .................. C07F 15/045 514/494 |
| 2016/0250618 A1* | 9/2016 | Long | ..................... B01J 20/226 423/648.1 |
| 2017/0096394 A1* | 4/2017 | Eddaoudi | ............... B01J 20/226 |
| 2017/0101429 A1* | 4/2017 | Yaghi | ..................... F17C 11/00 |
| 2017/0184531 A1* | 6/2017 | Snelders | .............. G01N 27/221 |

OTHER PUBLICATIONS

Howe, "Understanding Structure, Metal Distribution, and Water Adsorption in Mixed-Metal MOF-74" (Year: 2016).*
Bloch et al., "Gradual Release of Strongly Bound Nitric Oxide from $Fe_2(NO)_2(dobdc)$," *J. Am. Chem. Soc.*, 137, 3466, 2015.
Bloch et al., "Hydrocarbon separations in a metal-organic framework with open iron(II) coordination sites," *Science*, 335:1606-1610, 2012.
Bloch et al., "Reversible CO Binding Enables Tunable $CO/H_2$ and $CO/N_2$ Separations in Metal-Organic Frameworks with Exposed Divalent Metal Cations," *J. Am. Chem. Soc.*, 136, 10752, 2014.
Bloch et al., "Selective Binding of $O_2$ over $N_2$ in a Redox—Active Metal-Organic Framework with Open Iron(II) Coordination Sites," *J. Am. Chem. Soc.*, 133, 14814, 0211, 2011.
Britt et al., "Highly efficient separation of carbon dioxide by a metal-organic framework replete with open metal sites," *Proc. Natl. Acad. Sci. USA*, 106, 20637, 2009.
Caskey et al., "Dramatic Tuning of Carbon Dioxide Uptake via Metal Substitution in a Coordination Polymer with Cylindrical Pores," *J. Am. Chem. Soc.*, 130, 10870, 2008.
Chen et al., "Surface Interactions and Quantum Kinetic Molecular Sieving for $H_2$ and $D_2$ Adsorption on a Mixed Metal-Organic Framework Material," *J. Am. Chem. Soc.*, 130, 6411, 2008.

(Continued)

*Primary Examiner* — Christopher P Jones
(74) *Attorney, Agent, or Firm* — Parker Highlander PLLC

(57) ABSTRACT

A metal-organic framework (MOF) and uses thereof are provided herein, including an MOF comprising a repeat unit of the formula $[Zn_2(H_2O)L\cdot 0.5H_2O]_n$, wherein L is a ligand of the formula:

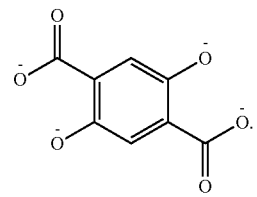

The MOFs provided herein may be used in the separation of two or more gaseous molecules from each other. In some embodiments, the gaseous molecules are carbon dioxide and acetylene.

13 Claims, 11 Drawing Sheets
(11 of 11 Drawing Sheet(s) Filed in Color)

(56) References Cited

OTHER PUBLICATIONS

Das et al., "Functional Mixed Metal-Organic Frameworks with Metalloligands," *Angew. Chem. Int. Ed.* 50, 10510, 2011.
Duan et al., "A new metal-organic framework with potential for adsorptive separation of methane from carbon dioxide, acetylene, ethylene, and ethane established by simulated breakthrough experiments," *J. Mater. Chem. A*, 2, 2628, 2014.
Duan et al., "Natural Gas Purification Using a Porous Coordination Polymer with Water and Chemical Stability," *Inorg. Chem.*, 54,4279, 2015.
Eguchi "Inverse and High $CO_2/C_2H_2$ Sorption Selectivity in Flexible Organic-Inorganic Ionic Crystals," *Angew. Chem. Int. Ed.*, 51, 1635, 2012.
Foo et al., "An Adsorbate Discriminatory Gate Effect in a Flexible Porous Coordination Polymer for Selective Adsorption of $CO_2$ over $C_2H_2$," *J. Am. Chem. Soc.*, 138, 3022, 2016.
He et al., "A series of metal-organic frameworks with high methane uptake and an empirical equation for predicting methane storage capacity," *Energy Environ. Sci.*, 6, 2735, 2013.
He et al., "Microporous metal-organic frameworks for storage and separation of small hydrocarbons," *Chem. Commun.*, 48, 11813, 2012.
Hu et al., "Microporous metal-organic framework with dual functionalities for highly efficient removal of acetylene from ethylene/acetylene mixtures," *Nat. Commun.*, 6, 7328, 2015.
Kong et al., "$CO_2$ Dynamics in a Metal-Organic Framework with Open Metal Sites," *J. Am. Chem. Soc.*, 134, 14341, 2012.
Li et al., "A rod-packing microporous hydrogen-bonded organic framework for highly selective separation of $C_2H_2/CO_2$ at room temperature," *Angew. Chem. Int. Ed.*, 54, 574, 2015.
Matsuda et al., "Highly controlled acetylene accommodation in a metal-organic microporous material," *Nature* 2005, 436, 238, 2005.
McDonald et al., "Capture of Carbon Dioxide from Air and Flue Gas in the Alkylamine-Appended Metal-Organic Framework mmen-$Mg_2$(dobpdc)," *J. Am. Chem. Soc.*, 134, 7056, 2012.
McDonald et al., "Cooperative insertion of $CO_2$ in diamine-appended metal-organic frameworks," *Nature*, 519, 303, 2015.
Nijem et al., "Molecular Hydrogen "Pairing" Interaction in a Metal Organic Framework System with Unsaturated Metal Centers (MOF-74)," *J. Am. Chem. Soc.*, 133, 4782, 2011.
Queen et al., "Comprehensive study of carbon dioxide adsorption in the metal-organic frameworks $M_2$ (dobdc) (M = Mg, Mn, Fe, Co, Ni, Cu, Zn)," *Chem. Sci.*, 5, 4569, 2014.
Rosi et al., "Rod Packings and Metal-Organic Frameworks Constructed from Rod-Shaped Secondary Building Units," *J. Am. Chem. Soc.*, 127, 1504, 2005.
Valvekens et al., "Metal-dioxidoterephthalate MOFs of the MOF-74 type: Microporous basic catalysts with well-defined active sites," *Journal of Catalysis*, 317, 1, 2014.
Vitillo et al., "Role of Exposed Metal Sites in Hydrogen Storage in MOFs," *J. Am. Chem. Soc.*, 130, 8386, 2008.
Wang et al., "Synthesis and Characterization of Metal-Organic Framework-74 Containing 2, 4, 6, 8, and 10 Different Metals," *Inorg. Chem.*, 53, 5881, 2014.
Wu et al., "High-Capacity Methane Storage in Metal-Organic Frameworks $M_2$(dhtp): The Important Role of Open Metal Sites," *J. Am. Chem. Soc.*, 131, 4995, 2009.
Xiang et al., "Open Metal Sites within Isostructural Metal-Organic Frameworks for Differential Recognition of Acetylene and Extraordinarily High Acetylene Storage Capacity at Room Temperature," *Angew. Chem. Int. Ed.* 49, 4615-4618, 2010.
Xiang et al., "Rationally tuned micropores within enantiopure metal-organic frameworks for highly selective separation of aceylene and ethylene," *Nat. Commun.* 2, 204, 2011.
Xu et al., "A microporous metal-organic framework with both open metal and Lewis basic pyridyl sites for highly selective $CH_2/CH_4$ and $C_2H_2/CO_2$ gas separation at room temperature," *J. Mater. Chem. A*, 1, 77, 2013.
Zhang et al., "Microporous metal-organic frameworks for acetylene storage and separation," *CrystEngComm*, 13, 5983, 2011.
Zhou et al., "Enhanced $H_2$ Adsorption in Isostructural Metal-Organic Frameworks with Open Metal Sites: Strong Dependence of the Binding Strength on Metal Ions," *J. Am. Chem. Soc.*, 130, 15268, 2008.

\* cited by examiner

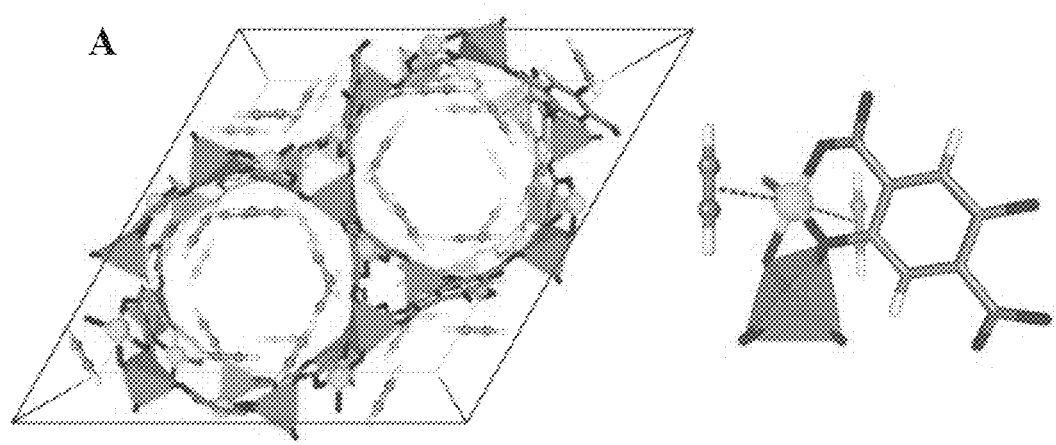
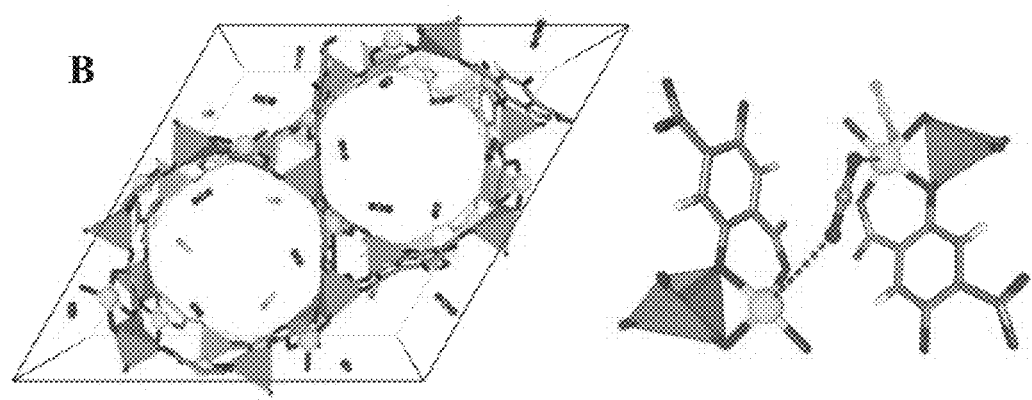
FIGS. 7A & 7B
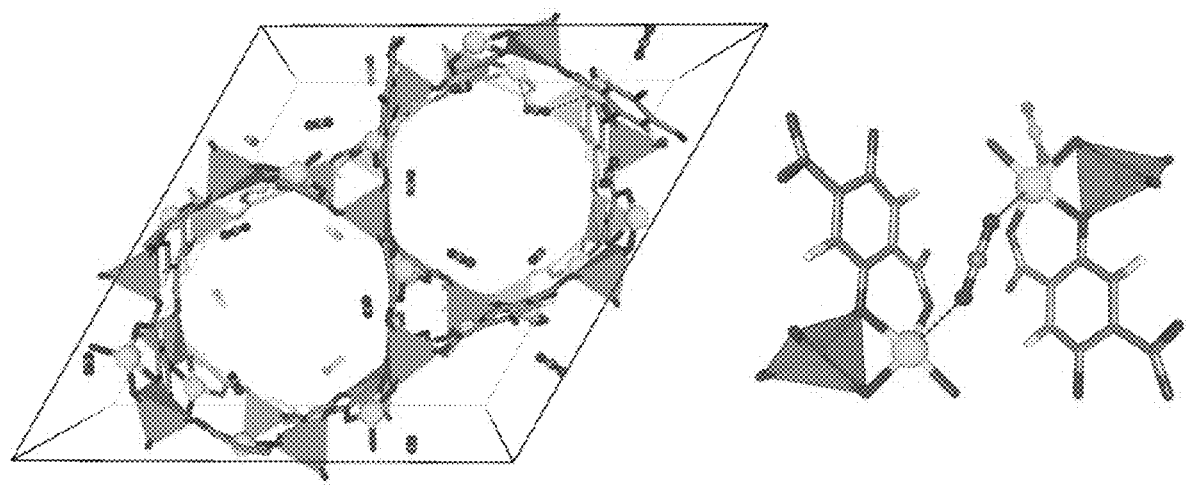
FIG. 8

UTSA-74: A METAL ORGANIC FRAMEWORK WITH TWO ACCESSIBLE BINDING SITES PER METAL CENTER FOR GAS SEPARATION AND GAS STORAGE

The present application claims the benefit of priority to U.S. Provisional Application No. 62/326,385, filed on Apr. 22, 2016, the entirety of which is incorporated herein by reference.

BACKGROUND

I. Field

The present disclosure relates generally to the fields of chemistry and materials science. More particularly, it concerns metal-organic frameworks, compositions thereof and methods use thereof, including for separating gas molecules such as ethylene and acetylene.

II. Description of Related Art

MOF-74 series are characteristic of the highest density of open metal sites on the ID channel pore surfaces of about 11 Å (Zhou, et al., 2008; Vitillo, et al., 2008; Queen, et al., 2014). Furthermore, different metal sites such as $Mg^{2+}$, $Zn^{2+}$, $Ni^{2+}$, $Co^{2+}$, $Mn^{2+}$, $Fe^{2+}$ and $Cu^{2+}$ can be systematically immobilized into their pore surfaces of the corresponding iso-structural MOFs for their different molecular recognition and/or chemical transformations (Nijem, et al., 2011; Wang, et al., 2014; Valvekens, et al., 2014). Accordingly, they have the record performance for the post-combustion carbon dioxide capture (Caskey, et al., 2008; Britt, et al., 2009; Kong, et al., 2012), acetylene (Xiang, et al., 2010) and methane storage (Wu, et al., 2009), and light hydrocarbon separations (Bloch, et al., 2012; He, et al., 2012) as well as some very specific gas separations such as $O_2/N_2$ (Bloch, et al., 2011), $CO/H_2$ and $CO/N_2$ (Bloch, et al., 2014) The open Fe(II) sites can be utilized as the co-catalytic sites for the oxidative transformation of ethane to ethanol (Xiao, et al., 2014) and the release of nitric oxide (Bloch, et al., 2015). The pores within MOF-74 are very robust, so they have been examined as the host materials to illustrate the gas sorption mechanisms through the adsorbate superlattice formation (Cho, et al., 2015). The open metal sites can be post-functionalized to tune the pores and to introduce functional sites, particularly amine sites, for their post-combustion carbon dioxide capture and separations (McDonald, et al., 2012; McDonald, et al., 2015). Its expanded organic linkers have also led to isoreticular MOFs whose pores are systematically enlarged up to about 100 Å for the encapsulation of enzyme molecules (Deng, et al., 2012). Because of the significance of this series of MOFs, the community has been wondering the possibility to construct new functional isomeric MOFs from the same organic linker 2,5-dioxido-1,4-benzenedicarboxylic acid but without success.

Ideal porous materials for column breakthrough gas separations are those which can not only take up large amount of preferred gas molecule but also display significantly high gas separation selectivity (Hu, et al., 2015). Those exhibiting high sieving effects can meet the high gas selectivity; however, their small pores typically limit their gas uptakes (Chen, et al., 2008; Xiang, et al., 2011; Das, et al., 2011). On the other hand, those taking up large amount of gas molecules generally have comparatively low gas separation selectivity (Bloch, et al., 2012; He, et al., 2012). This is the so-called trade-off between physical adsorption capacity and selectivity of porous materials, a daunting challenge to developing porous materials for gas separations. One particular example of where this challenge is evident is $C_2H_2/CO_2$ separation. This separation is challenging given the fact that these two gas molecules have very similar shapes, dimensions (332×334×570 pm versus 318.9×333.9×536.1 pm) and boiling points (−84° C. versus −78.5° C.). Such a separation is important to get high purity of acetylene for its commercial usage (Zhang, et al., 2011). As such, new metal-organic frameworks which may be used to separate different gas molecules are needed.

SUMMARY

In some aspects, the present disclosure provides MOFs which may be used to remove one type of molecules from a mixture. In some aspects, the present disclosure provides metal-organic frameworks comprising a repeating unit of the formula: $[M_2L]_n$, wherein: M is a divalent metal ion and L is a ligand of the formula:

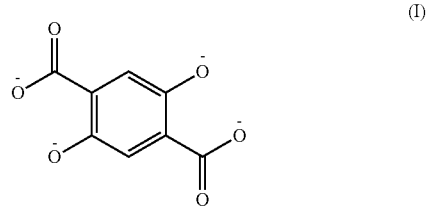

(I)

comprising a rhombohedral unit cell of a: 22.9 Å±5% (or 21.755 to 24.04 Å), b: 22.9 Å±5% (or 21.755 to 24.04 Å), and c: 15.9 Å±5% (or 15.1 to 16.7 Å); or a hydrate thereof. In some embodiments, the metal-organic frameworks further comprise a repeating unit of the formula: $[M_2L]_n$, wherein: M is a divalent metal ion and L is a ligand of the formula:

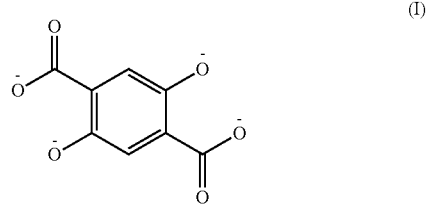

(I)

comprising a rhombohedral unit cell of a: 22.8 to 23.0 Å, b: 22.8 to 23.0 Å, and c: 15.8 to 16.0 Å; or a hydrate thereof.

In some embodiments, M is a divalent transition metal ion such as $Zn^{2+}$. In some embodiments, the metal-organic frameworks comprise a powder X-ray diffraction spectrum having a peak at 7.709°2θ using CuKα radiation. In some embodiments, the powder X-ray diffraction spectrum further comprises peaks at 14.262 and 15.454°2θ. In some embodiments, the powder X-ray diffraction spectrum further comprises 3 or more peaks at 11.981, 13.373, 14.262, 15.454, 18.427, 19.599, 20.271, 20.49, 22.794, 23.27, 24.096, 25.054, 27.656, and 28.055°2θ. In some embodiments, the powder X-ray diffraction pattern further comprises peaks at 11.981, 13.039, 13.373, 14.262, 15.454, 16.232, 17.032, 18.427, 19.599, 20.271, 20.49, 21.089, 22.484, 22.794, 22.837, 23.27, 24.096, 24.363, 25.054, 25.59, 26.25, 26.556, 26.933, 27.398, 27.656, 27.892, 28.055, 28.752, 28.787, 29.57, 29.811, and 30.031°2θ. In some embodiments, the powder X-ray diffraction pattern further comprises peaks at 7.117, 10.5, 11.981, 13.039, 13.373, 14.262, 15.454, 16.232, 16.711, 17.032, 18.427, 18.719, 19.599, 20.271, 20.49, 21.089, 21.464, 22.484, 22.794, 22.837, 23.076, 23.27, 24.096, 24.363, 25.054, 25.59, 26.25, 26.556, 26.933, 27.398, 27.656, 27.892, 28.055, 28.752, 28.787, 29.468, 29.57, 29.811, and 30.031°2θ.

In some embodiments, the rhombohedral unit cell is a: 22.9-22.98 Å, b: 22.9-22.98 Å, and c: 15.86-15.92 Å. In some embodiments, the rhombohedral unit cell is 22.917, 22.917, and 15.902; 22.956, 22.956, and 15.883; or 22.951, 22.951, and 15.897. In some embodiments, the metal-organic framework has a R-3c space group.

In some embodiments, the metal-organic frameworks are a hydrate. In some embodiments, the metal-organic frameworks are a hemihydrate. In some embodiments, the metal-organic frameworks further comprise a water molecule in each repeating unit. In some embodiments, the formula of the repeating unit is $[M_2(H_2O)L]_n$. In some embodiments, the repeating unit is $[Zn_2(H_2O)L]_n$, $[Zn_2L]_n$, or $[Zn_2(H_2O)L]_n \cdot 0.5H_2O$. In yet another aspect, the present disclosure provides methods of preparing a metal-organic framework comprising admixing a metal salt and a ligand of the formula:

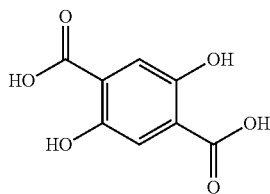

(II)

to form a reaction mixture in an aqueous organic solvent at a temperature from about 120° C. to about 200° C. for a time period from about 12 hours to about 7 days.

In some embodiments, the temperature is from about 140° C. to about 170° C. such as about 158° C. In some embodiments, the aqueous organic solvent is a mixture of N,N'-dimethylformamide (DMF) and water. In some embodiments, the mixture comprises from about 10:1 v/v to about 50:1 v/v DMF to water such as about 30:1 v/v DMF to water.

In some embodiments, the time period is from about 24 hours to about 96 hours such as about 72 hours. In some embodiments, the metal salt is a divalent metal salt. In some embodiments, the metal salt is a divalent metal salt hydrate. In some embodiments, the metal salt is a zinc salt. In some embodiments, the metal salt is $Zn(NO_3)_2 \cdot 6H_2O$.

In some embodiments, the reaction mixture is heated to the temperature at a rate of about 1° C. per minute. In some embodiments, the metal organic framework is activated by heating under vacuum to a temperature from about 150° C. to about 300° C. such as about 200° C. In some embodiments, the methods comprise heating for a time period of about 1 hour to about 12 hours. In some embodiments, the time period is about 2 hours.

In still yet another aspect, the present disclosure provides metal-organic frameworks prepared according to the methods described herein.

In yet another aspect, the present disclosure provides methods of separating two or more compounds using a metal organic framework comprising:

(A) obtaining a metal-organic framework described herein;
(B) combining the metal-organic framework with a mixture comprising a first compound and one or more second compounds; and
(C) separating the first compound from the one or more second compounds based upon their differential sorption rate within the metal-organic framework.

In some embodiments, the compounds are gas molecules. In some embodiments, the first compound is an alkyne$_{(C \leq 8)}$ such as acetylene. In some embodiments, the second compound is carbon dioxide. In some embodiments, the mixture comprises from about 1:999 to about 1:1 of the first compound to the second compound. In some embodiments, the mixture comprises about 1:99 the first compound to the second compound.

In some embodiments, the separation is carried out at a pressure of about 100 kPa. In some embodiments, the metal-organic framework is adhered to a fixed bed surface. In some embodiments, an absorber is packed with the metal-organic framework. In some embodiments, the absorption is carried out at a temperature from about 0° C. to about 75° C. such as at about room temperature.

In still yet another aspect, the present disclosure provides methods wherein the metal-organic framework described herein is used in an application selected from sensing, heterogeneous catalysis, drug delivery, lithium sulfide battery, membranes, and analytical devices.

In yet another aspect, the present disclosure provides metal-organic frameworks comprising a repeating unit of the formula: $M_2L$, wherein: M is a divalent metal ion and L is a ligand of the formula:

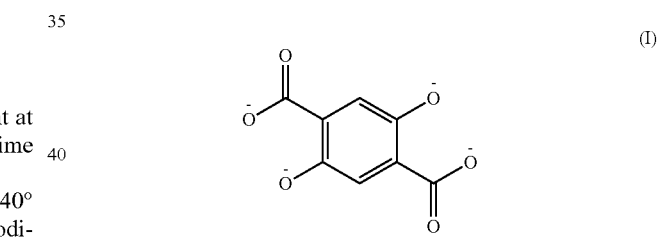

(I)

comprising at least one M ion having a tetrahedral coordination geometry; or a hydrate thereof.

In some embodiments, M is a divalent transition metal ion such as $Zn^{2+}$. In some embodiments, one of the M atoms is in a tetrahedral coordination geometry. In some embodiments, the second M atom is in an octahedral coordination geometry. In some embodiments, the first M atom is in the tetrahedral coordination geometry and the second M atom is in the octahedral coordination geometry.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

(FIG. 1E) the highlighted octahedral Zn2 (yellow ball) bound by two axial water molecules; and (FIG. 1F) of the activated UTSA-74a in which two axial water molecules can be completely removed, generating accessible open Zn2 sites (yellow balls) which can potentially bind two gas molecules per metal center on the pore surfaces of the 1D channels of about 8.0 Å.

FIGS. 5A & 5B shows the $N_2$ adsorption isotherms at 77K and the pore distribution of UTSA-74a.

FIGS. 7A & 7B show the DFT-D optimized structure of (FIG. 7A) UTSA-74⊃$C_2H_2$ and (FIG. 7B) x-ray single crystal structure of UTSA-74⊃$CO_2$ in which the local coordination environments are shown at the right.

FIG. 8 shows the DFT-D optimized structure of UTSA-74⊃$CO_2$ in which the local coordination environments are shown at the right.

FIG. 10A shows the heats of adsorption of both $C_2H_2$ and $CO_2$ in UTSA-74a and FIG. 10B shows the comparison of the heats of adsorption of $C_2H_2$ among UTSA-74a and other MOFs.

(FIG. 11B) comparison of % $C_2H_2$ in the exit gas for beds packed with HOF-3, Zn-MOF-74, UTSA-74a, ZJU-60a, and PCP-33 plotted as a function of the dimensionless time; (FIG. 11C) comparison of the moles of $C_2H_2$ captured per L of material during the interval for which the product gas is 99.95% $CO_2$, plotted as a function of the dimensionless breakthrough time, $\tau_{break}$.

FIG. 14 shows the experimental column breakthrough curve for an equimolar $C_2H_2/CO_2$ mixture (298 K, 1 bar) in an adsorber bed packed with UTSA-74a.

DESCRIPTION OF ILLUSTRATIVE EMBODIMENTS

Figures 1A, 1B, 1C, 1D, 1E, 1F:
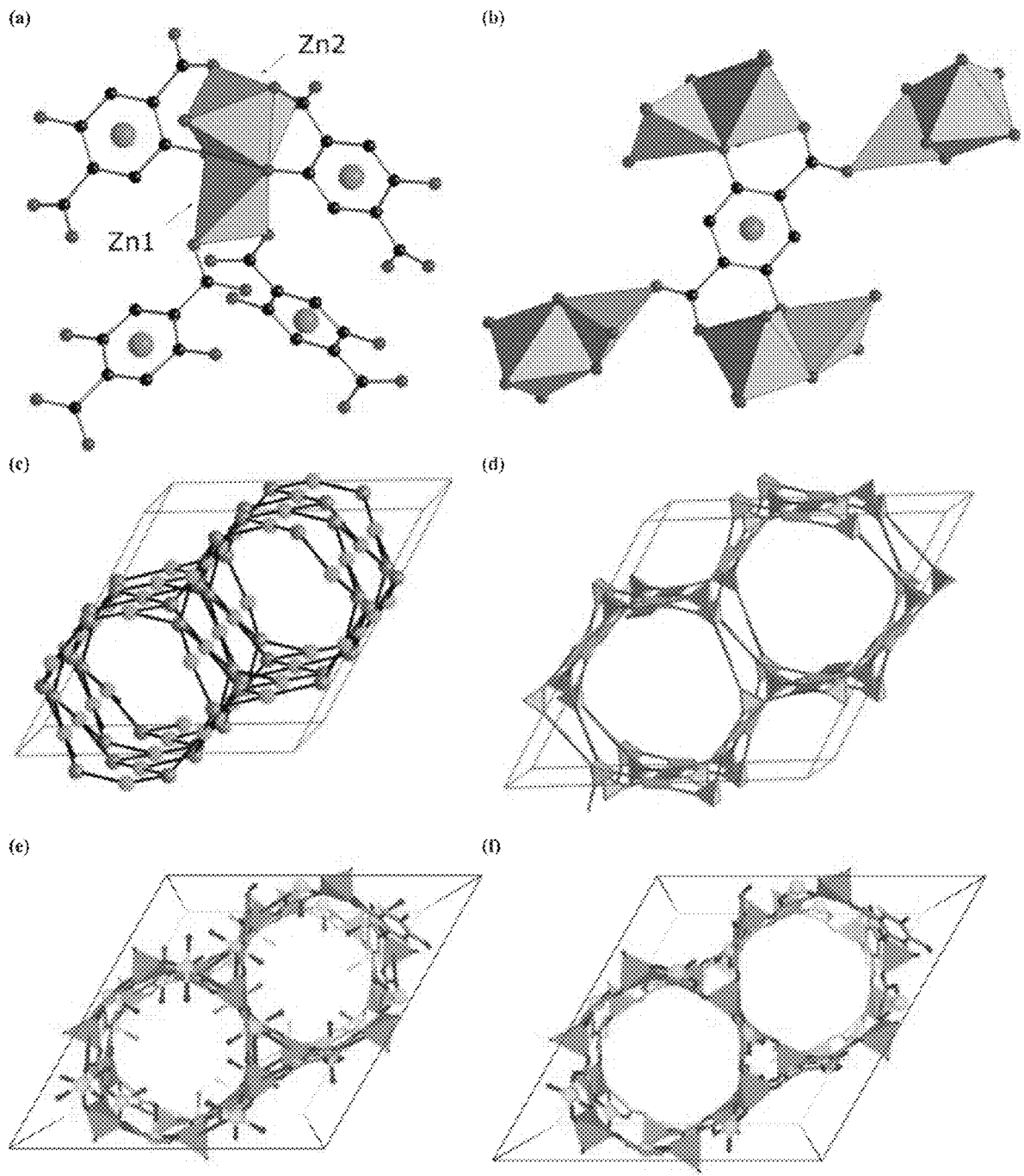
FIGS. 1A-1F show single crystal x-ray structures of the as-synthesized VISA-74 indicating (FIG. 1A) the binuclear $Zn_2(O)_2(CO_2)_4$ secondary building unit (one $Zn^{2+}$ is in a tetrahedral coordination while another one is in an octahedral coordination) acts as the four coordinated node, (FIG. 1B) the organic linker dobdc$^{4-}$ as the second four coordinated node, to form (FIG. 1C) and (FIG. 1D) a three-dimensional framework of the novel fgl topology (the light blue ball and tetrahedron represent $Zn_2(O)_2(CO_2)_4$ node while light green ball and square represent dobdc$^{4-}$ node)

Provided herein are metal-organic frameworks of the formula: $M_2L$ wherein L is 2,5-dioxido-1,4-benzenedicarboxylic acid which shows two metal ion binding sites for guest gas molecules. These metal-organic frameworks may be used to separate one gas molecule from a mixture of two or more gas molecules such as carbon dioxide and acetylene. In some embodiments, the metal-organic framework is an isomeric form of the Zn-MOF-74 which comprises a rhombohedral unit cell with unit cell dimensions: a is 22.9±0.1 Å, b is 22.9±0.1 Å, and c is 15.9±0.1 Å.

I. Definitions

"Metal-organic frameworks" (MOFs) are framework materials, typically three-dimensional, self-assembled by the coordination of metal ions with organic linkers exhibiting porosity, typically established by gas adsorption. The MOFs discussed and disclosed herein are at times simply identified by their repeat unit as defined below without brackets or the subscript n. A mixed-metal-organic frameworks (M'MOF) is a subset of MOFs having two of more types of metal ions.

The term "unit cell" is basic and least volume consuming repeating structure of a solid. The unit cell is described by its angles between the edges (α, β, γ) and the length of these edges (a, b, c). As a result, the unit cell is the simplest way to describe a single crystal X-ray diffraction pattern.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerization, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc. Note that for MOFs the repeat unit may also be shown without the subscript n.

"Pores" or "micropores" in the context of metal-organic frameworks are defined as open space within the MOFs; pores become available, when the MOF is activated for the storage of gas molecules. Activation can be achieved by heating, e.g., to remove solvent molecules.

"Multimodal size distribution" is defined as pore size distribution in three dimensions.

"Multidentate organic linker" is defined as ligand having several binding sites for the coordination to one or more metal ions.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Additionally, it is contemplated that one or more of the metal atoms may be replaced by another isotope of that metal. In some embodiments, the zinc atoms can be $^{64}Zn$, $^{66}Zn$, $^{67}Zn$, $^{68}Zn$, or $^{70}Zn$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on a carbon atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

The term "saturated" when referring to an atom means that the atom is connected to other atoms only by means of single bonds.

The above definitions supersede any conflicting definition in any of the reference that is incorporated herein by reference. The fact that certain terms are defined, however, should not be considered as indicative that any term that is undefined is indefinite. Rather, all terms used are believed to describe the invention in terms such that one of ordinary skill can appreciate the scope and practice the present invention.

Example 1: Methods and Materials

A. Materials and Physical Measurements

The commercial chemicals are used as purchased from Alfa. Thermogravimetric analysis (TG) was performed by a TGA Q500 thermal analysis system. All TGA experiments were performed under a $N_2$ atmosphere from 40-800° C. at a rate of 5° C./min. Data were analyzed using the TA Universal Analysis software package. X-ray powder diffraction were collected by a Broker AXSD8 Discover powder diffractometer at 40 kV, 40 mA for Cu K$\alpha$, ($\lambda$=1.5406 Å).

The gas sorption isotherms were collected on a Belsorp-max. Ultrahigh-purity-grade (>99.999%) $N_2$, $CO_2$, and $C_2H_2$ gases were used in this adsorption measurement. To maintain the experimental temperatures liquid nitrogen (77 K) and temperature-programmed water bath (273 and 298 K) were used respectively.

B. X-Ray Crystallography

X-ray diffraction data were collected on a Bruker-AXS SMART Breeze CCD diffractometer at 296 K for UTSA-74 and UTSA-74a and 120 K for UTSA-74⊃$CO_2$ using graphite monochromated MoK$\alpha$ radiation ($\lambda$=0.71073 Å). Preparation of UTSA-74⊃$CO_2$ crystals: The as-synthesized crystals of UTSA-74 were placed into the sample holder and activated to remove solvent molecules in situ using the gas adsorption apparatus Belsorp-max at 200° C. under high vacuum for two hours to generate the crystals of activated UTSA-74a. Gradual loading of $CO_2$ into the UTSA-74a sample up to 100 kPa at 298 K leads to the formation of crystals of UTSA-74⊃$CO_2$, which were transferred into glove box, and sealed into the capillary tubes under $CO_2$ atmosphere. The data reduction included a correction for Lorentz and polarization effects, with an applied multi-scan absorption correction (SADABS). The crystal structure was solved and refined using the SHELXTL program suite. Direct methods yielded all non-hydrogen atoms, which were refined with anisotropic thermal parameters. All hydrogen atom positions were calculated geometrically and were riding on their respective atoms. The SQUEEZE subroutine of the PLATON software (Spek, 2001) suite was used to remove the scattering from the highly disordered guest molecules. CCDC 1046717-1046719 contains the supplementary crystallographic data of UTSA-74, UTSA-74a, and UTSA-74⊃$CO_2$, respectively. These data can be obtained free of charge from the Cambridge Crystallographic Data Centre via www.ccdc.cam.ac.uk/data_request/cif.

C. Dual Langmuir Freundlich Parameter Fits and Equations $$q = q_{A,sat} \frac{b_A p^{v_A}}{1 + b_A p^{v_A}} + q_{B,sat} \frac{b_B p^{v_B}}{1 + b_B p^{v_B}} \quad (1)$$

with T-dependent parameters $b_A$, and $b_B$ $$b_A = b_{A0} \exp\left(\frac{E_A}{RT}\right); \quad (2)$$
$$b_B = b_{B0} \exp\left(\frac{E_B}{RT}\right)$$

The parameters are provided in Table 1.

TABLE 1

Dual-Langmuir-Freundlich parameter fits for $C_2H_2$, and $CO_2$ in UTSA-74a.

| | Site A | | | | Site B | | | |
|---|---|---|---|---|---|---|---|---|
| | $q_{A, sat}$ mol kg$^{-1}$ | $b_{A0}$ Pa$^{-v_i}$ | $E_A$ kJ mol$^{-1}$ | $v_A$ dimensionless | $q_{B, sat}$ mol kg$^{-1}$ | $b_{B0}$ Pa$^{-v_i}$ | $E_B$ kJ mol$^{-1}$ | $v_B$ dimensionless |
| $C_2H_2$ | 0.7 | 1.81 × 10$^{-16}$ | 60.2 | 1.8 | 6.2 | 2.30 × 10$^{-7}$ | 20.7 | 0.66 |
| $CO_2$ | 4.8 | 2.02 × 10$^{-12}$ | 37 | 1 | 2.4 | 5.37 × 10$^{-6}$ | 2 | 1 |

D. Isosteric Heat of Adsorption.

The binding energies of $C_2H_2$, and $CO_2$ in UTSA-74a are reflected in the isosteric heat of adsorption, $Q_{st}$, defined as $$Q_{st} = RT^2 \left( \frac{\partial \ln p}{\partial T} \right)_q \quad (3)$$

These values were determined using the pure component isotherm fits.

E. IAST Calculations of Adsorption Selectivities.

In order to establish the feasibility of $C_2H_2/CO_2$ separations we performed calculations using the Ideal Adsorbed Solution Theory (IAST) of Myers and Prausnitz.

To determine the adsorption selectivity, $S_{ads}$, defined for separation of a binary mixture of species i and j by $$S_{ads} = \frac{q_i / q_j}{p_i / p_j} \quad (4)$$

where the $q_i$ represent the molar loadings of component i that is in equilibrium with a bulk gas phase with partial pressures $p_i$ in the mixture.

F. Transient Breakthrough Simulations.

The performance of industrial fixed bed adsorbers is dictated by a combination of adsorption selectivity and uptake capacity. For a proper comparison of various MOFs, we perform transient breakthrough simulations using the simulation methodology described in the literature. For the breakthrough simulations, the following parameter values were used: length of packed bed, L=0.3 m; voidage of packed bed, $\varepsilon$=0.4; superficial gas velocity at inlet, u=0.04 m/s. The framework density of UTSA-74a is 1401 kg m$^{-3}$. The breakthrough time, $\tau_{break}$, is define as the time at which the exit gas contains<0.05%=500 ppm $C_2H_2$. The amount of $C_2H_2$ captured during the time interval 0-$\tau_{break}$ can be determined from a material balance. These amounts, expressed as moles $C_2H_2$ captured per L of framework material, are plotted against $\tau_{break}$ in Table 2.

TABLE 2

Breakthrough calculations for separation of 50/50 $C_2H_2/CO_2$ mixture at 298 K.

| | Dimensionless breakthrough time $\tau_{break}$ | $C_2H_2$ adsorbed during 0-$\tau_{break}$ mol L$^{-1}$ |
|---|---|---|
| UTSA-74a | 362 | 4.86 |
| UTSA-60a | 173 | 2.33 |
| PCP-33 | 308 | 4.16 |

TABLE 2-continued

Breakthrough calculations for separation of 50/50 $C_2H_2/CO_2$ mixture at 298 K.

| | Dimensionless breakthrough time $\tau_{break}$ | $C_2H_2$ adsorbed during 0-$\tau_{break}$ mol L$^{-1}$ |
|---|---|---|
| HOF-3 | 52 | 0.7 |
| ZnMOF-74 | 302 | 4.06 |

Example 2: Synthetic Methods

Synthesis of UTSA-74. A mixture of H$_4$dobdc (0.099 g, 0.50 mmol), Zn(NO$_3$)$_2$.6H$_2$O (0.149 g, 0.50 mmol), N,N'-dimethylformamide (DMF, 6.0 mL), and H$_2$O (0.20 mL) was placed in a Teflon-lined stainless steel vessel (12 mL) and heated at a rate of 1° C. min$^{-1}$ to 158° C., and kept at that temperature for 72 hours, and then it was cooled to room temperature at a rate of 0.1° C. min$^{-1}$. Subsequently, yellow rod-shaped crystals were obtained in 89% yield based on Zn(NO$_3$)$_2$.6H$_2$O. Elemental analysis: Calcd. for Zn$_2$(H$_2$O)(dobdc).0.5(H$_2$O)(C$_8$H$_5$O$_{7.5}$Zn$_2$: C, 27.30; H, 1.43; N, 0.00; Found: C, 27.21; H, 1.47; N: 0.06.

Example 3: Discussion

UTSA-74 was synthesized at a high temperature of 158° C. instead of 105° C. for the synthesis of Zn-MOF-74 (Rosi, et al., 2005). Control of the solvent mixture ratio, particularly the water amount, is also important to get high purity UTSA-74.

Single crystal X-ray diffraction reveals that UTSA-74 crystallizes in rhombohedral, R-3c space group and exhibits a three-dimensional porous framework with regular 1D channels along c direction. (See Table 3) There exist two crystallographically independent Zn$^{2+}$ sites. Zn1 site is four-coordinated by two dobdc$^{4-}$ carboxylate oxygen atoms and two dobdc$^{4-}$ hydroxyl oxygen atoms, creating a tetrahedral geometry. Zn2 site shows six-coordinated octahedral geometry, completed by four dobdc$^{4-}$ oxygen atoms (two carboxylate oxygen atoms plus two hydroxyl oxygen atoms) in the equatorial plane, and two terminal coordinated water molecules in the axis orientation (FIG. 1A) Because these terminal water molecules can be possibly removed during thermal and/or vacuum activation, each of these Zn2 sites can presumably bind two gas molecules. Without consideration of these terminal solvent molecules, UTSA-74 has an effective 1D aperture of about 8.0 Å and the potential solvent-accessible volume of UTSA-74 estimated by Platon program is 3474.9 Å$^3$ per unit cell volume 7272.9 Å$^3$, equal to 47.8% of the cell volume (Spek, 2001). Compared with Zn-MOF-74 which has a 58.2% accessible pore space, UTSA-74 has a slightly more condensed structure.

TABLE 3

Crystallographic Data of UTSA-74, UTSA-74a, and UTSA-74 ⊃ CO$_2$

| | Compounds | | |
|---|---|---|---|
| | UTSA-74 | UTSA-74a | UTSA-74 ⊃ CO$_2$ |
| Empirical formula | C$_{24}$H$_{12}$O$_{21}$Zn$_6$ | C$_{24}$H$_6$O$_{18}$Zn$_6$ | C$_{27}$H$_6$O$_{24}$Zn$_6$ |
| Formula weight | 1028.79 | 974.51 | 1106.54 |
| Temperature (K) | 296(2) | 296(2) | 120(2) |
| Wavelength (Å) | 0.71073 | 0.71073 | 0.71073 |
| Crystal system, space group | Rhombohedral, R-3c | Rhombohedral, R-3c | Rhombohedral, R-3c |
| Unit cell dimensions (Å) | a = b = 22.9170(4), c = 15.9024(5) | a = b = 22.9556(13), c = 15.883(2) | a = b = 22.9511(8), c = 15.8965(11) |
| Volume (Å$^3$) | 7232.8(3) | 7248.2(12) | 7251.7(6) |
| Z, Calculated density (Mg/m$^3$) | 12, 1.409 | 6, 1.34 | 6, 1.52 |

TABLE 3-continued

Crystallographic Data of UTSA-74, UTSA-74a, and UTSA-74⊃CO$_2$

| | Compounds | | |
|---|---|---|---|
| | UTSA-74 | UTSA-74a | UTSA-74⊃CO$_2$ |
| F(000) | 2988 | 2844 | 3240 |
| Crystal size (mm) | 0.18 × 0.08 × 0.08 | 0.18 × 0.08 × 0.08 | 0.18 × 0.08 × 0.08 |
| Theta range for data collection | 2.76-27.51 | 2.76-26.00 | 2.42-27.64 |
| Completeness to theta | 99.6% | 99.6% | 97.3% |
| GOF | 1.215 | 0.915 | 1.282 |
| Final R indices [I > 2sigma(I)] | $R_1 = 0.0772$, $\omega R_2 = 0.1717$ | $R_1 = 0.1221$, $\omega R_2 = 0.2445$ | $R_1 = 0.1631$, $\omega R_2 = 0.3024$ |

Figure 2:
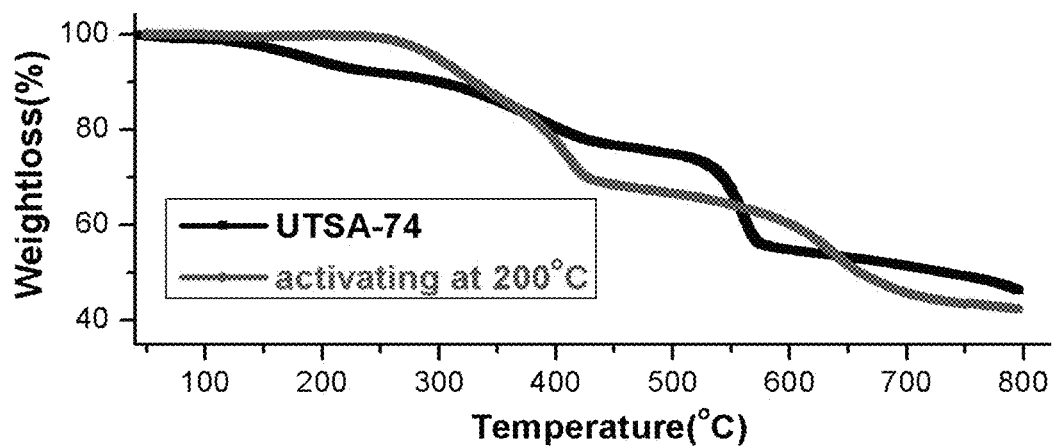
FIG. 2 shows the TG plots of as-synthesized samples and activated samples of UTSA-74.
Figure 3:
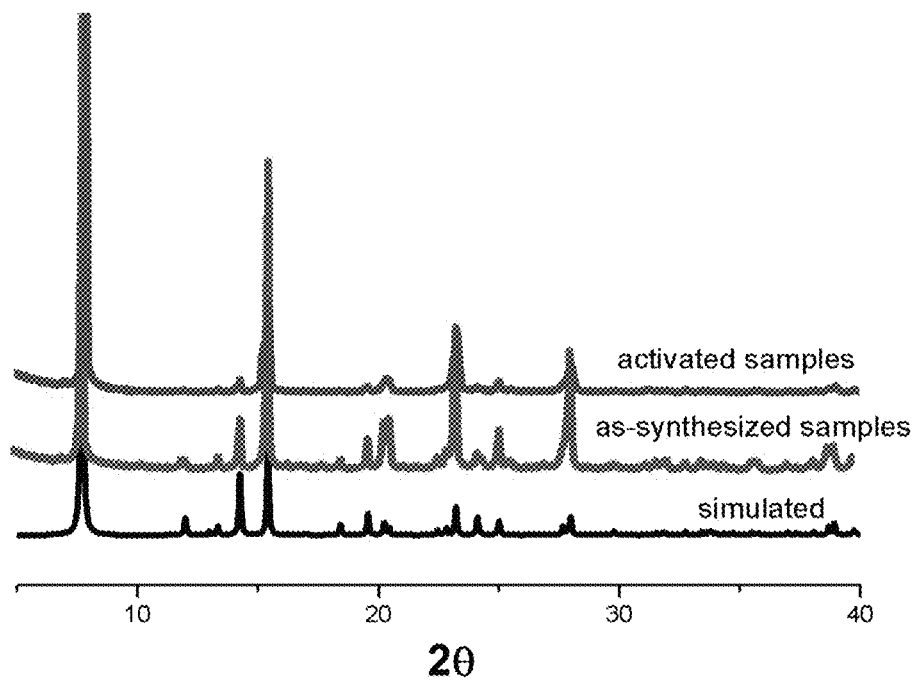
FIG. 3 shows the PXRD patterns of as-synthesized and activated samples of UTSA-74, as well as the simulated PXRD patterns calculated from the single crystal data of UTSA-74.
Figures 4A, 4B:
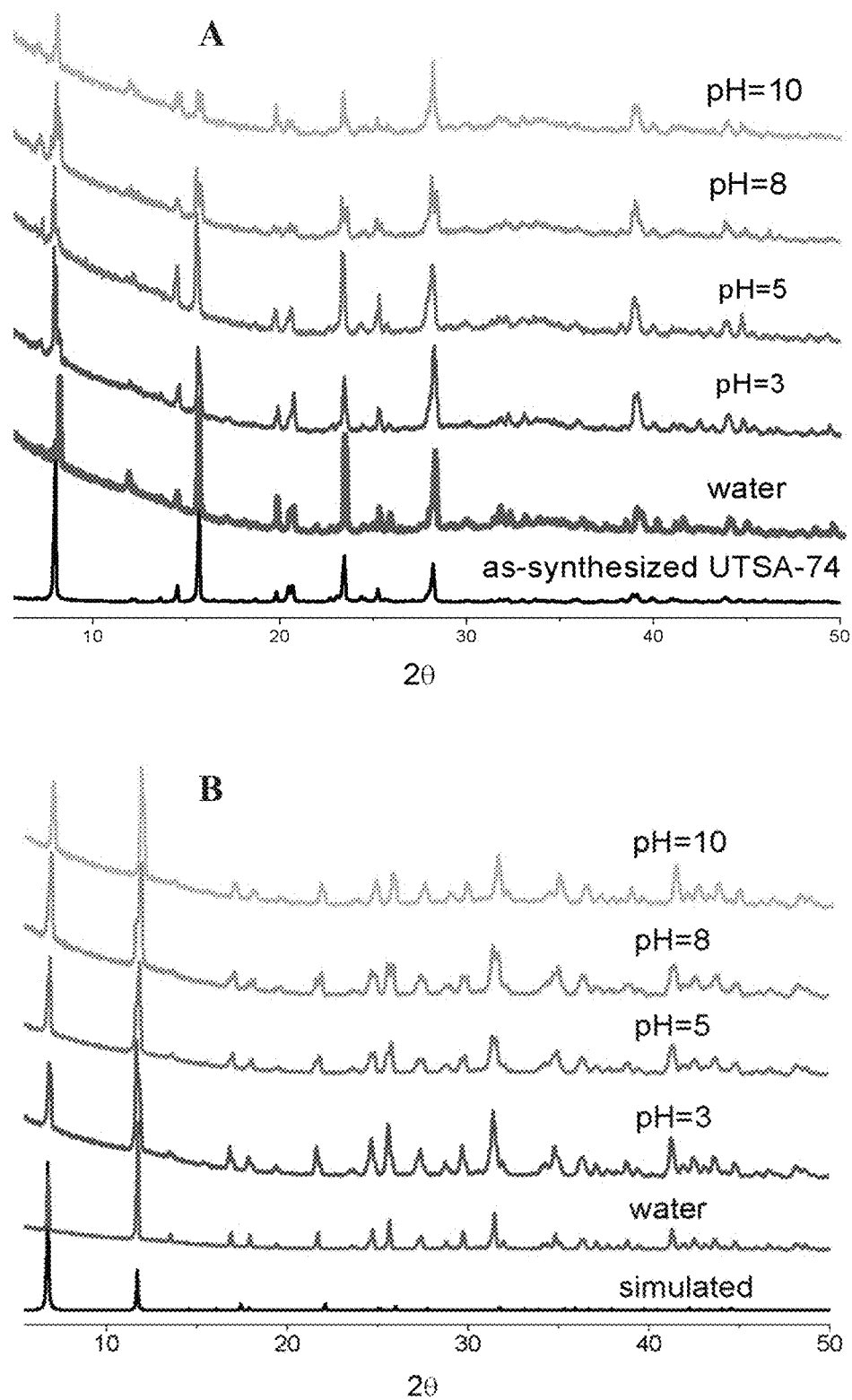
FIGS. 4A & 4B show the PXRD patterns of UTSA-74 and Zn-MOF-74 after immerging in water with the pH values in the range of 3 to 10 for 24 h, respectively (UTSA-74 (FIG. 4A); Zn-MOF-74 (FIG. 4B)).

The purity of the bulk products was determined by comparison of the simulated and experimental PXRD patterns and further supported by elemental analysis and thermogravimetric analysis (FIGS. 2-4). TGA reveals that the solvent molecules and coordinated water molecules can be removed by activating at 200° C. (see FIG. 2 and FIG. 3). UTSA-74 can thus be easily activated at 200° C. under high vacuum to provide open metal sites on the pore surface channels of the resulting UTSA-74a, as evidenced by single crystal X-ray diffraction study (FIG. 1F). The structure of UTSA-74a clearly indicates that each Zn2 potentially can bind two gas molecules. This structural feature is unusual in MOF structures but has been demonstrated in porous M'MOFs from metalloligands (Chen, et al., 2008; Xiang, et al., 2011; Das, et al., 2011). The stability of UTSA-74 is comparable to Zn-MOF-74, as shown in their PXRDs after immersion in water of variable pH values in the range of 3 to 10 (FIG. 4).

Figures 5A, 5B:
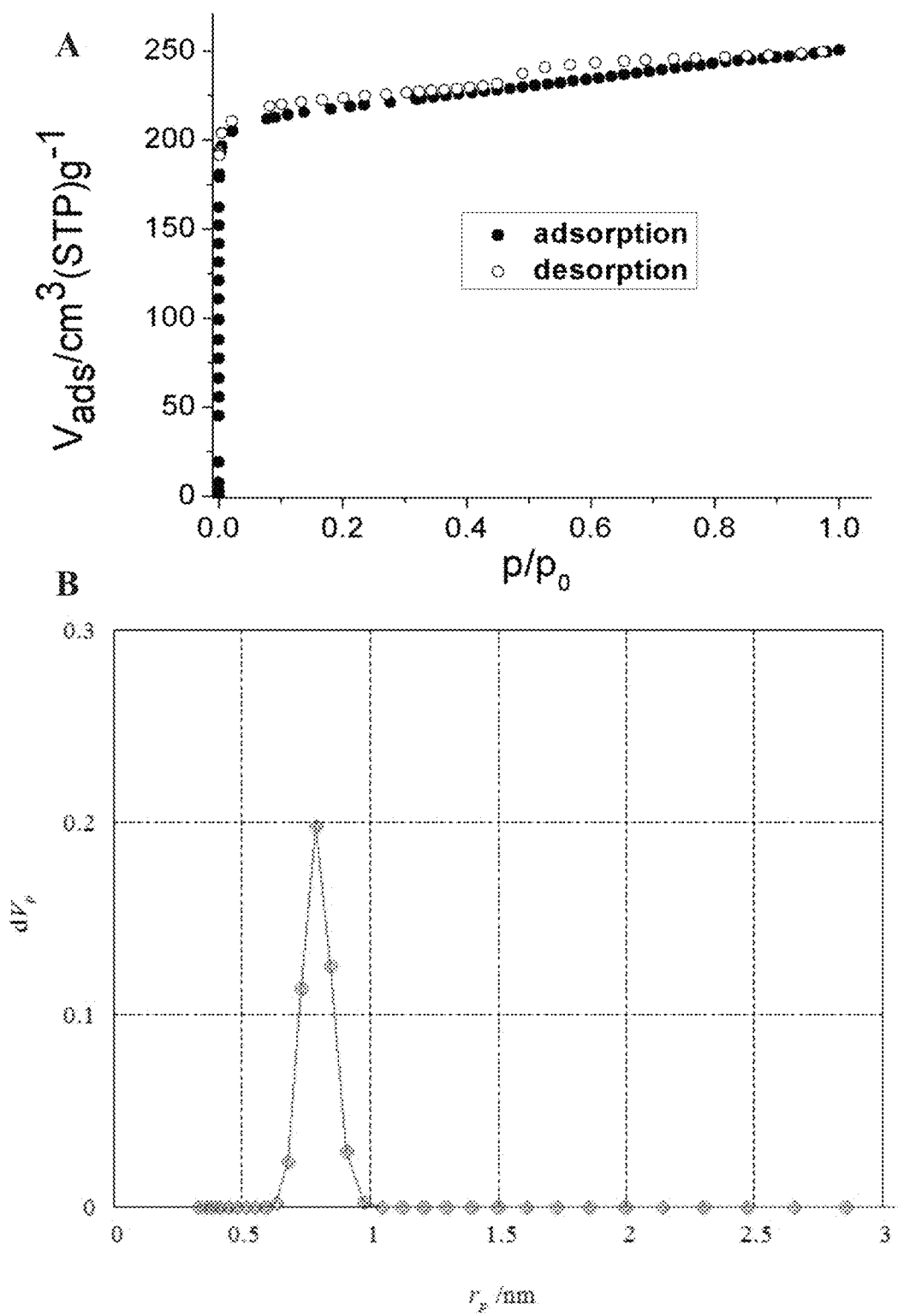

The permanent porosity of UTSA-74a was confirmed by N$_2$ adsorption at 77K (FIG. 5), exhibiting a fully reversible type-I isotherm. UTSA-74a has a BET surface area of 830 m$^2$/g (Langmuir surface area of 996 m$^2$/g), a uniform pore size of 0.80 nm, and a total pore volume of 0.39 cm$^3$/g. Compared with Zn-MOF-74, UTSA-74a is less porous in terms of both pore volume and pore size.

Figure 6:
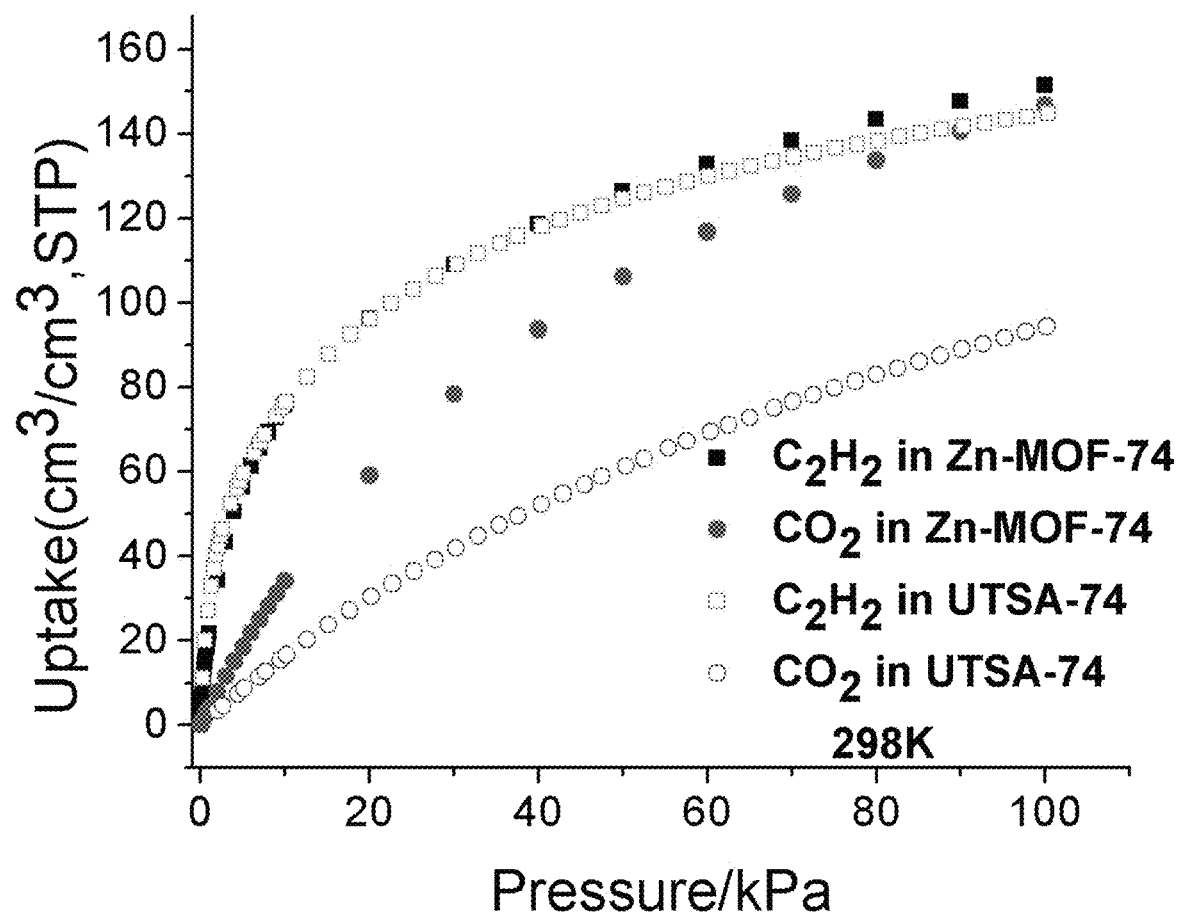
FIG. 6 shows a comparison of sorption isotherms of $C_2H_2$ and $CO_2$ for UTSA-74 and Zn-MOF-74 at 298 K.

The C$_2$H$_2$ and CO$_2$ gas sorption isotherms of UTSA-74a were examined at ambient temperature of 298 K and pressure of 100 kPa in order to figure out its potential for gas storage and separation. As expected, UTSA-74a takes up a large amount of C$_2$H$_2$ (145.0 cm$^3$/cm$^3$), which is comparable to 150 cm$^3$/cm$^3$ in Zn-MOF-74 (FIG. 6) (Xiang, et al., 2010). However, UTSA-74a adsorbs much less amount of CO$_2$ (95.0 cm$^3$/cm$^3$) than Zn-MOF-74 of 146 cm$^3$/cm$^3$, which is only about ⅔ of the CO$_2$ uptake in Zn-MOF-74 (Caskey, et al., 2008; Britt, et al., 2009; Kong, et al., 2012)

In order to understand the unique sorption performance of UTSA-74a for C$_2$H$_2$ and CO$_2$, detailed dispersion-corrected density-functional theory (DFT-D) calculations were performed (Giannozzi, et al., 2009). The coordination configuration of the open Zn$^{2+}$ site was found to be quite sensitive to gas adsorption. In the DFT-D optimized bare UTSA-74a structure, the open Zn$^{2+}$ and its four coordinating O are not in an ideal planar configuration, similar to what the experimental SXRD structure suggests. The slightly distorted ZnO$_4$ forms a pseudo-tetrahedral configuration, representing a natural way to minimize the coordination unsaturation of the Zn$^{2+}$ ion. Upon gas adsorption, the ZnO$_4$ in the optimized MOF structure becomes notably more planar, with Zn fully exposed on both sides of the ZnO$_4$ plane, and consequently, maximizes its direct interactions with guest molecules (FIG. 7A). For C$_2$H$_2$ adsorption in UTSA-74a, the calculation shows that the open Zn directly binds to C≡C (toward the acetylene molecule center), similar to C$_2$H$_2$ adsorption in Zn-MOF-74 (Xiang, et al., 2010). For a single C$_2$H$_2$ adsorption on the Zn site, the calculated static binding energy ($E_B$) is ~43.9 kJ/mol, comparable to what found in Zn-MOF-74 (~43.8 kJ/mol, obtained using the same approach). When the metal sites are heavily populated, each pair of C$_2$H$_2$ molecules adsorbed on two neighboring open Zn sites in UTSA-74a are close to each other (with a H . . . C distance of ~3.3 Å), leading to beneficial intermolecular interaction through H$^{\delta+}$ . . . C$^{\delta-}$ hydrogen bonding (FIG. 7A). Consequently, the calculated average static adsorption energy of C$_2$H$_2$ increased notably to 49.0 kJ/mol. For CO$_2$, the binding on the open-Zn in UTSA-74a is of a side-on fashion, similar to the case of CO$_2$ adsorption in Zn-MOF-74 (Zhou, et al., 2008; Vitillo, et al., 2008; Queen, et al., 2014). In these calculation, two possible adsorption configurations were considered. In the first configuration, each CO$_2$ binds to two neighboring open M sites simultaneously (FIG. 8), and the DFT-D calculated static binding energy is ~33.4 kJ/mol. Without wishing to be bound by any theory, it is believed that at high CO$_2$ loading, the binding configuration may shift to one CO$_2$ per metal, which doubles the uptake when saturated, and maximizes the overall framework-guest interaction. In this case, the average $E_B$ decreases (by ~10%) to ~30.0 kJ/mol. This means that at low CO$_2$ loading, the former configuration is energetically preferred, which is experimentally confirmed by the x-ray single crystal structure of UTSA-74⊃CO$_2$ (FIG. 7B). Overall, the CO$_2$ binding strength is comparable to what was found in Zn-MOF-74 (~31.7 kJ/mol).

The calculation results are fully consistent with the experimental results that the C$_2$H$_2$ adsorption capacity in UTSA-74a is nearly equal to the C$_2$H$_2$ adsorption capacity in Zn-MOF-74, as C$_2$H$_2$ adsorption is mainly determined by the open metal sites and the two structures have similar density of adsorptions sites on open metals. Furthermore, the calculation results also agree with the experimental findings of distinct adsorption amount for C$_2$H$_2$ and CO$_2$ in UTSA-74a at room temperature and 100 kPa (n(C$_2$H$_2$):n(CO$_2$) ~1.5), and relatively smaller difference at 273 K and 100 kPa (n(C$_2$H$_2$):n(CO$_2$)~1.2), as at room temperature the binding of CO$_2$ molecule towards open metal site adopts the first configuration of each CO$_2$ binding to two neighboring open M sites simultaneously, which results in moderate loading of CO$_2$, whereas at 273 K, the low temperature likely helps to shift the CO$_2$ binding toward the second configuration of one CO$_2$ per metal, which consequently increases the loading of CO$_2$. Moreover, based on the calculation, the closest contacts between C$_2$H$_2$ molecules within the 1D channel is ~3.3 Å (H . . . C distance), indicative of a dense molecular packing after loading C$_2$H$_2$, whereas adjacent CO$_2$ molecules were largely separated by ca. 7.5 Å (O . . . O distance), indicative of a very loose packing after lower loading of CO$_2$. In contrast, in Zn-MOF-74, (Zhou, et al., 2008; Vitillo, et al., 2008; Queen, et al., 2014; Xiang, et al., 2010) the separation for both $C_2H_2$ and $CO_2$ molecules is comparable, such as $C_2H_2$ with a distance of ~4.4 Å and $CO_2$ with a ~3.6 Å O . . . O distance. These results explain the different $C_2H_2/CO_2$ selectivity between UTSA-74a and Zn-MOF-74.

Figures 9A, 9B:
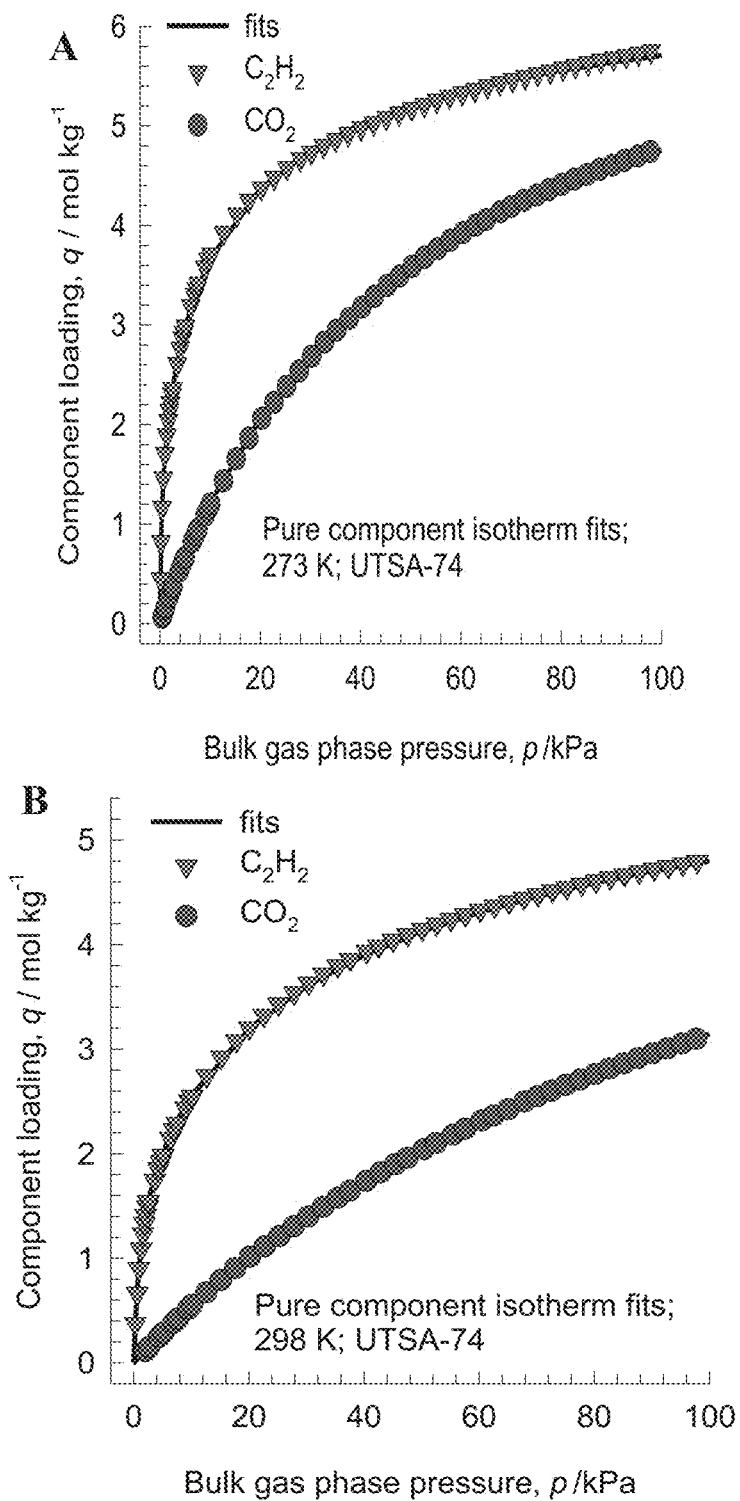
FIGS. 9A & 9B show the comparison of absolute component loadings for $C_2H_2$, and $CO_2$ at (FIG. 9A) 273 K, and (FIG. 9B) 298 K in UTSA-74a with the isotherm fits. The experimentally measured excess loadings for $C_2H_2$, and $CO_2$ at temperatures of 273 K, and 298 K in UTSA-74a were fitted with the dual-Langmuir-Freundlich isotherm model
Figures 10A, 10B:
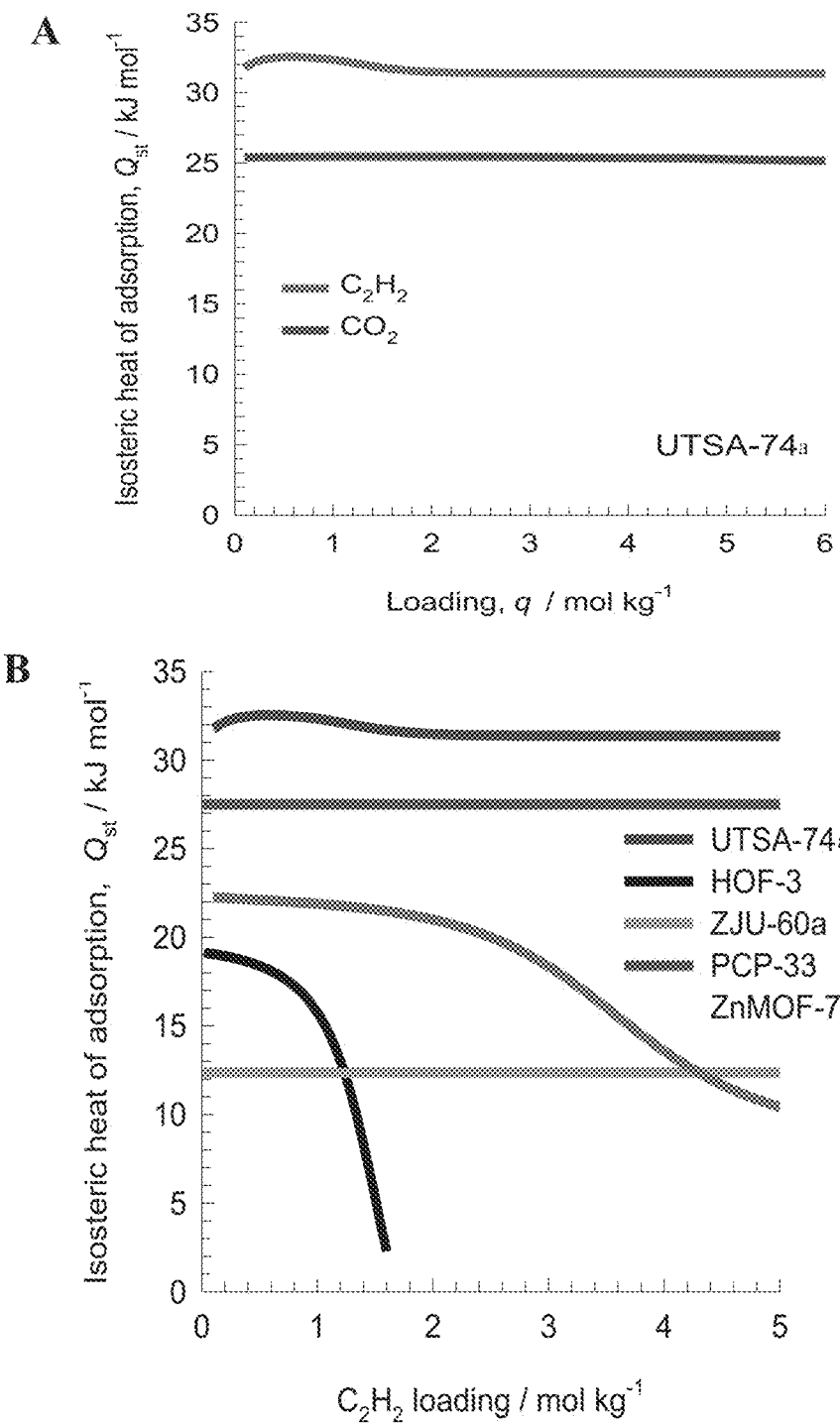
FIGS. 10A & 10B show the heat of adsorption of different gas molecules.

Next, to evaluate the experimental adsorption energies of $C_2H_2$, and $CO_2$ in UTSA-74a, the calculation of isosteric heats of adsorption ($Q_{st}$), based on pure component isotherms of them at 298 K and 273 K (FIG. 9), is carried out using the Clausius-Clapeyron equation (Dincă and Long, 2005; Yang, et al., 2009). FIG. 10A presents data on the loading dependence of $Q_{st}$ for $C_2H_2$ and $CO_2$. The obtained $Q_{st}$ value for $C_2H_2$ is above 31 kJ/mol, which is bigger than the value for $CO_2$ of 25 kJ/mol. The results agree well with that the guest-host interactions between $C_2H_2$ and UTSA-74a fairly exceed that between $CO_2$ and UTSA-74a. Moreover, the $Q_{st}$ value is also compared with other MOFs. The results is shown in FIG. 10B, giving the hierarchy of UTSA-74a>PCP-33 (Duan, et al., 2015)>Zn-MOF-74 (Xiang, et al., 2010)>ZJU-60a (Duan, et al., 2014)≈HOF-3 (Li, et al., 2015), is indicative of superior affinity of UTSA-74a toward $C_2H_2$.

Figures 11A, 11B:
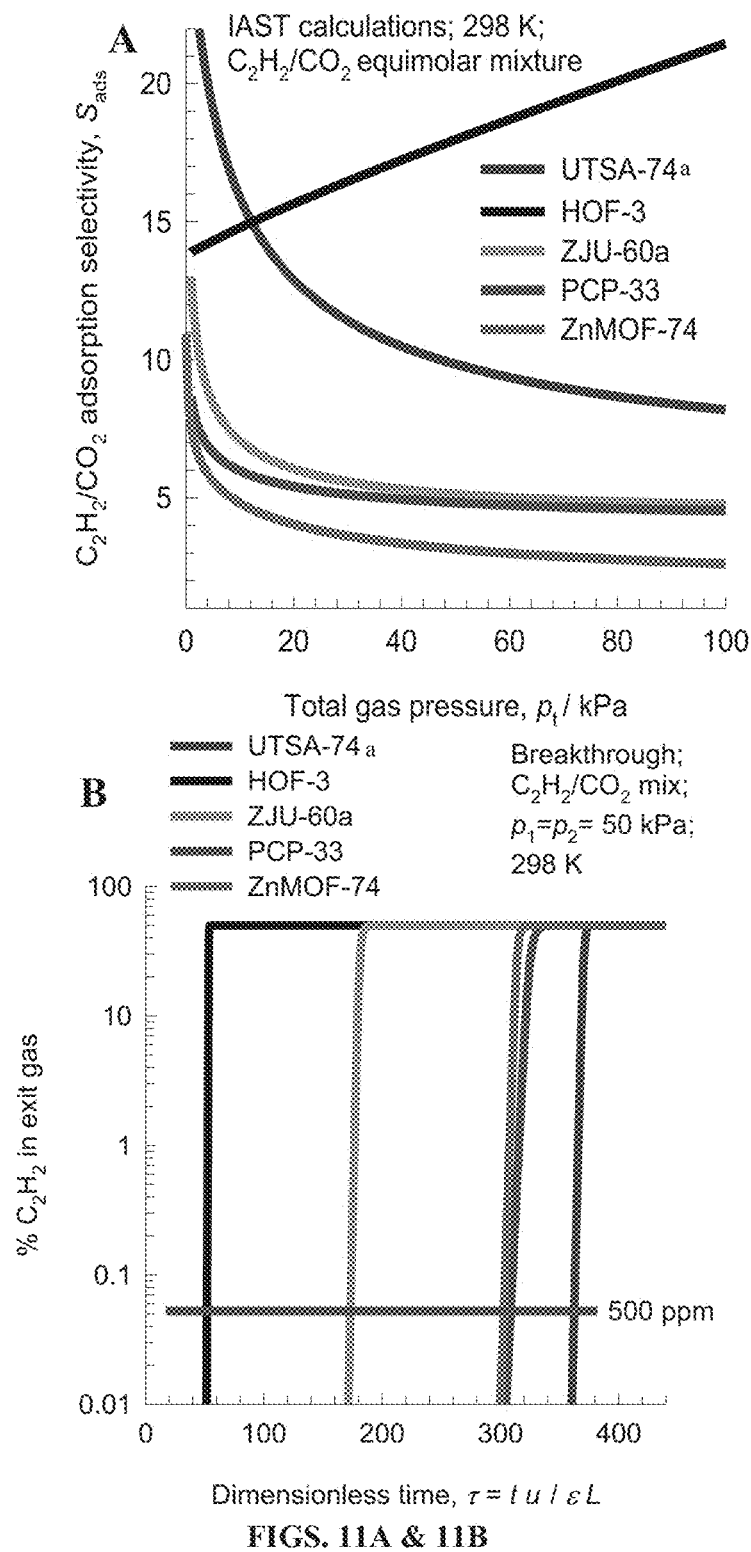
FIGS. 11A-11C show (FIG. 11A) IAST adsorption selectivities of $C_2H_2/CO_2$ in equimolar mixture among UTSA-74a and other MOFs at 298 K.
Figure 12:
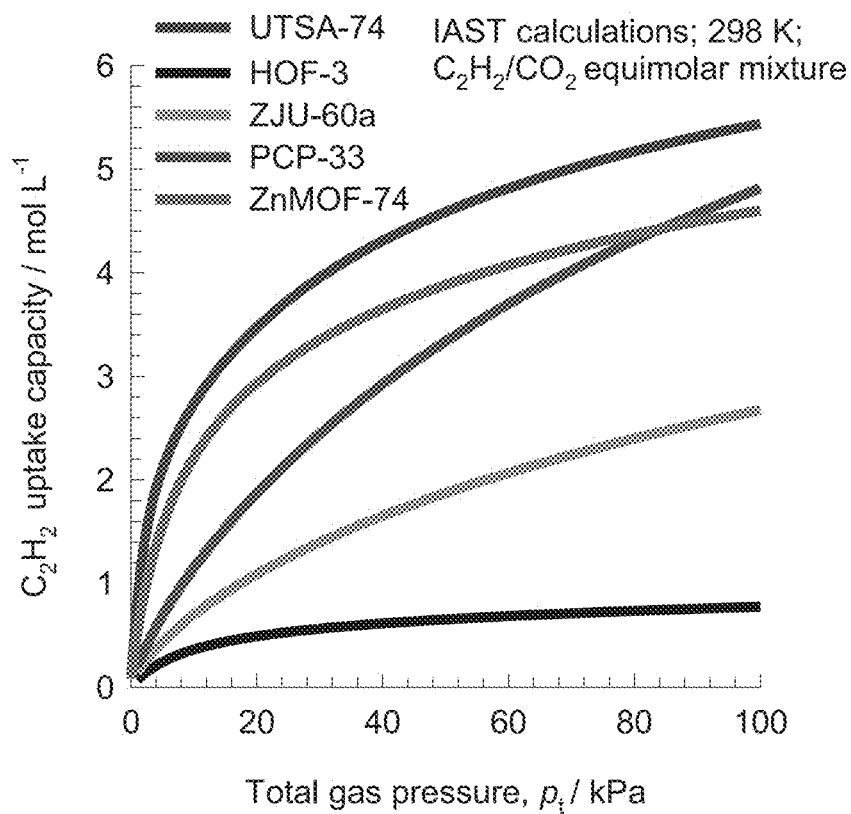
FIG. 12 shows the LAST calculations of uptake capacity of $C_2H_2$, for separation of 50/50 $C_2H_2/CO_2$ mixture at 298 K using HOF-3, UTSA-74a, ZJU-60a, and PCP-33.

To obtain the potential in separation of $C_2H_2/CO_2$ by means of UTSA-74a, firstly, the commonly used approach upon the calculation by using the ideal adsorbed solution theory (IAST) is adopted (Myers and Prausnitz, 1965; Krishna and Long, 2011; Krishna, 2014; Krishna and Baur, 2003). As shown in FIG. 11A, the simulated adsorption selectivity ($S_{ads}$) for the $C_2H_2/CO_2$ binary equimolar mixture is above twenty at low pressure, even more than best in class HOF-3; but, with the increase of pressure it gradually decreases down to nine at 100 kPa. However, the $S_{ads}$ values at ambient pressure still fairly exceed those observed in other MOFs such as PCP-33, Zn-MOF-74, ZJU-60a (less than five). The results support the potential in practical procedure of $C_2H_2/CO_2$, separation that in principle requests $S_{ads}$ more than eight. The hierarchy of $S_{ads}$ values at 100 kPa is HOF-3>UTSA-74a>ZJU-60a≈PCP-33>MOF-74. Further, the performance of PSA units is also dictated by the uptake capacity. The component loading of $C_2H_2$, $q_1$, can be determined from IAST. The hierarchy of uptake capacities at 100 kPa, expressed as the number of moles of $C_2H_2$ adsorbed per L of adsorbent, is UTSA-74a>Zn-MOF-74≈PCP-33>ZJU-60a>HOF-3 (FIG. 12), suggesting that the adsorption capacity of specific molecule would also determine the finally separation performance of MOFs.

Figure 11C:
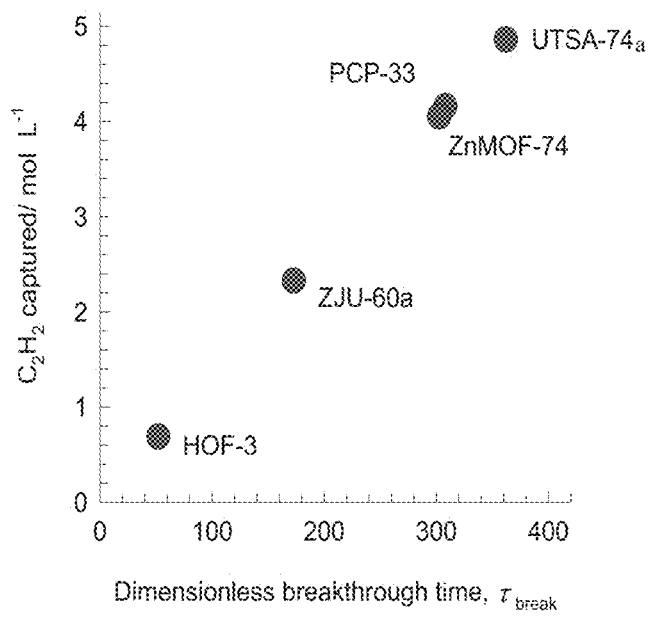
Figure 13:
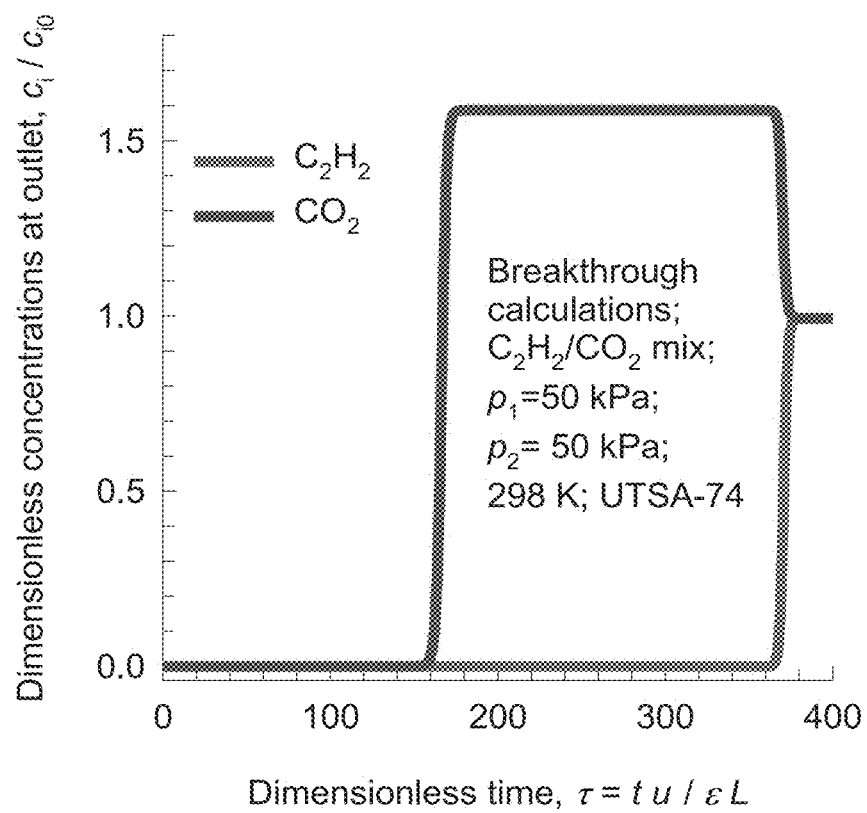
FIG. 13 shows the transient breakthrough simulations for separation of equimolar $C_2H_2/CO_2$ mixture using UTSA-74a at 298 K, with partial pressures of 50 kPa each.

In order to properly evaluate the combined effects of selectivity and capacity, transient breakthrough simulations using the simulation methodology were carried out as described in the literature (Duan, et al., 2015; Duan, et al., 2014; Li, et al., 2015; Myers and Prausnitz, 1965; Krishna and Long, 2011; Krishna, 2014; Krishna and Baur, 2003). The simulations in FIG. 13 demonstrate the UTSA-74a is of potential use for this challenging separation of $C_2H_2/CO_2$ mixtures. During the initial transience, the effluent gas contains pure $CO_2$ and this continues until $C_2H_2$ starts breaking through because its uptake capacity in UTSA-74a has been reached. FIG. 11B and FIG. 11C presents a comparison of $C_2H_2/CO_2$ separation performance with UTSA-74a, Zn-MOF-74, HOF-3, ZJU-60a, and PCP-33, resulting in the hierarchy of HOF-3<ZJU-60a<Zn-MOF-74≈PCP-33<UTSA-74a. On the other hand, it is noted that the amount of $C_2H_2$ capture capacities have the following hierarchy, UTSA-74a>PCP-33≈Zn-MOF-74>ZJU-60a>HOF-3. Thereby, the excellent separation characteristics of UTSA-74a should be due to a combination of high selectivity (FIG. 11A) and high $C_2H_2$ uptake capacity (FIG. 6), The poor performance of HOF-3 is due to its low $C_2H_2$ uptake capacity (47 cm$^3$/g at 296 K and 100 kPa), which further means that the low capacity cannot compensate for the high selectivity with this material.

Figure 14:
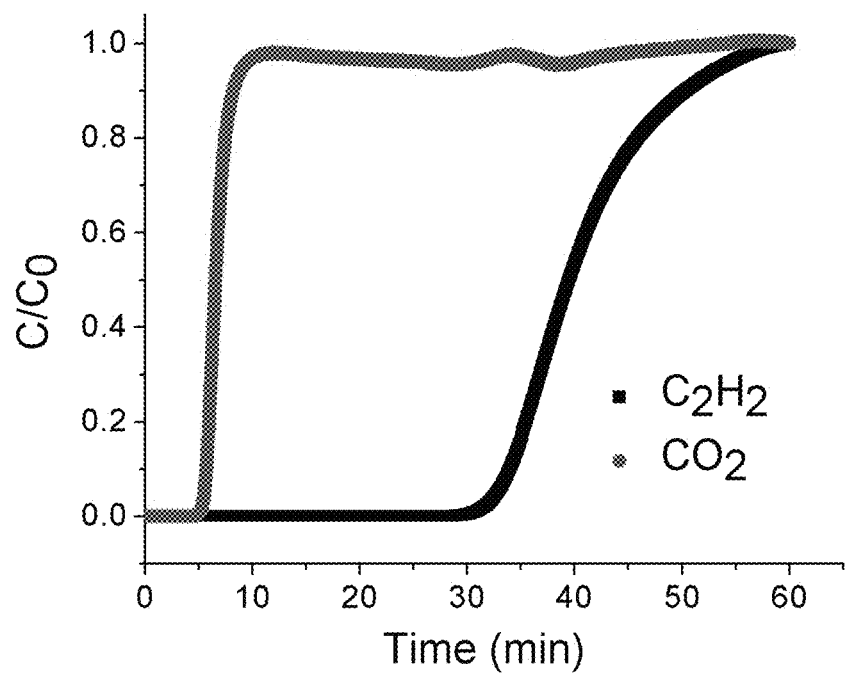

To establish the $C_2H_2/CO_2$ separation performance of UTSA-74 in practice, breakthrough experiments were also run in which an equimolar $C_2H_2/CO_2$ mixture was flowed over a packed column of activated UTSA-74a solid with a total flow of 2 cm$^3$/min at 298 K. The result is shown in FIG. 14, suggesting complete separation of $C_2H_2$ from the equimolar $C_2H_2/CO_2$ mixture by a column packed with activated UTSA-74a solid. The performance of UTSA-74a for $C_2H_2/CO_2$ separation is much more efficient than HOF-3, as clearly demonstrated in their separation factors of 20.1 and 2.04, respectively, determined through experimental breakthrough. UTSA-74a is a porous MOFs whose separation for $C_2H_2/CO_2$ mixture has been clearly established by experimental breakthrough (Matsuda, et al., 2005; He, et al., 2012; Xu, et al., 2013; Eguchi, et al., 2012; Foo, et al., 2016).

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

Bloch et al. *J. Am. Chem. Soc.*, 136, 10752, 2014.
Bloch et al., *J. Am. Chem. Soc.*, 133, 14814, 0211, 2011.
Bloch et al., *J. Am. Chem. Soc.*, 137, 3466, 2015.
Bloch et al., *Science*, 335, 1606, 2012.
Britt et al., *Proc. Natl. Acad. Sci. USA*, 106, 20637, 2009.
Caskey et al., *J. Am. Chem. Soc.*, 130, 10870, 2008.
Chen et al., *J. Am. Chem. Soc.*, 130, 6411, 2008.
Cho et al., *Nature*, 527, 503, 2015.
Das et al., *Angew. Chem. Int. Ed.*, 50, 10510, 2011.
Deng et al., *Science*, 336, 1018, 2012.
Dincă and Long, *J. Am. Chem. Soc.*, 127, 9376, 2005.
Duan et al., *Inorg. Chem.*, 54, 4279, 2015.
Duan et al., *J. Mater. Chem. A*, 2, 2628, 2014.
Eguchi *Angew. Chem. Int. Ed.*, 51, 1635, 2012.
Foo et al., *S. J. Am. Chem. Soc.*, 138, 3022, 2016.
Giannozzi et al., *J. Phys. Condens. Matter*, 21, 395502, 2009
He et al., *Energy Environ. Sci.*, 10, 9107, 2012.
He *Chem. Common.*, 48, 10856, 2012.
Hu *Nat. Commun.*, 6, 7328, 2015.
Kong *J. Am. Chem. Soc.*, 134, 14341, 2012.
Krishna, R. *Microporous Mesoporous Mater*, 185, 30, 2014.
Krishna and Baur, *Sep. Purif. Technol.*, 33, 21, 2003
Krishna and Long, *J. Phys. Chem. C*, 115, 12941, 2011.
Li et al., *Angew. Chem. Int. Ed.*, 54, 574, 2015.
Matsuda et al., Y. *Nature* 2005, 136, 238, 2005.
McDonald et al., *J. Am. Chem. Soc.*, 134, 7056, 2012.
McDonald et al., *Nature*, 519, 303, 2015.
Myers and Prausnitz, *AIChE J.* 11, 121, 1965.

Nijem et al., *J. Am. Chem. Soc.*, 133, 4782, 2011.
Queen et al., *Chem. Sci.*, 5, 4569, 2014.
Rosi et al., *J. Am. Chem. Soc.*, 127, 1504, 2005.
Spek, A. L. *PLATON*, 2001.
Valvekens et al. *Journal of Catalysis*, 317, 1, 2014
Vitillo et al., *J. Am. Chem. Soc.*, 130, 8386, 2008.
Wang et al., *Inorg. Chem.*, 53, 5881, 2014.
Wu et al., *J. Am. Chem. Soc.*, 131, 4995, 2009.
Xiang et al., B. *Nat. Commun.*, 2, 204, 2011.
Xiang et al., *Angew. Chem., Int. Ed.*, 49, 4615.
Xiao et al., *Nat. Chem.*, 6, 590, 2014.
Xu et al., *J. Mater. Chem. A*, 1, 77, 2013.
Yang et al., *Nat. Chem.*, 1, 487, 2009.
Zhang et al., *CrystEngComm*, 13, 5983, 2011.
Zhou et al., *J. Am. Chem. Soc.*, 130, 15268, 2008.

What is claimed is:

1. A metal-organic framework comprising a repeating unit of the formula: $[M_2L]_n$, wherein: M is a divalent metal ion and L is a ligand of the formula:

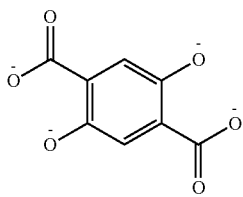

(I)

comprising a rhombohedral unit cell of a: 22.9 Å±5%, b: 22.9 Å±5%, and c: 15.9 Å±5%; or a hydrate thereof.

2. The metal-organic framework of claim 1 comprising a repeating unit of the formula: $[M_2L]_n$, wherein: M is a divalent metal ion and L is a ligand of the formula:

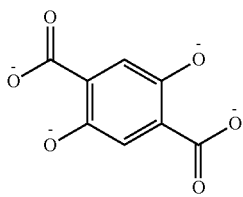

(I)

comprising a rhombohedral unit cell of a: 22.8 to 23.0 Å, b: 22.8 to 23.0 Å, and c: 15.8 to 16.0 Å; or a hydrate thereof.

3. The metal-organic framework of claim 1, wherein M is $Zn^{2+}$.

4. The metal-organic framework of claim 1, wherein the metal-organic framework comprises a powder X-ray diffraction spectrum having a peak at 7.709° 2θ using CuKα radiation.

5. The metal-organic framework of claim 4, wherein the powder X-ray diffraction spectrum further comprises peaks at 14.262 and 15.454° 2θ.

6. The metal-organic framework of claim 5, wherein the powder X-ray diffraction pattern further comprises peaks at 7.117, 10.5, 11.981, 13.039, 13.373, 14.262, 15.454, 16.232, 16.711, 17.032, 18.427, 18.719, 19.599, 20.271, 20.49, 21.089, 21.464, 22.484, 22.794, 22.837, 23.076, 23.27, 24.096, 24.363, 25.054, 25.59, 26.25, 26.556, 26.933, 27.398, 27.656, 27.892, 28.055, 28.752, 28.787, 29.468, 29.57, 29.811, and 30.031° 2θ.

7. The metal-organic framework of claim 1, wherein the rhombohedral unit cell is 22.917, 22.917, and 15.902; 22.956, 22.956, and 15.883; or 22.951, 22.951, and 15.897.

8. The metal-organic framework of claim 1, wherein the metal-organic framework is a hydrate.

9. The metal-organic framework of claim 8, wherein the metal-organic framework is a hemihydrate.

10. The metal-organic framework of claim 1, wherein the metal-organic framework further comprises a water molecule in each repeating unit.

11. A method of separating two or more compounds using a metal organic framework comprising:

(A) obtaining a metal-organic framework of claim 1;

(B) combining the metal-organic framework with a mixture comprising a first compound and one or more second compounds; and (C) separating the first compound from the one or more second compounds based upon their differential sorption rate within the metal-organic framework.

12. The method of claim 11, wherein the first compound is acetylene.

13. The method of claim 11, wherein the second compound is carbon dioxide.

* * * * *